United States Patent
Jain

(10) Patent No.: US 10,362,432 B2
(45) Date of Patent: Jul. 23, 2019

(54) SPATIALLY AMBIENT AWARE PERSONAL AUDIO DELIVERY DEVICE

(71) Applicant: EmbodyVR, Inc., Redwood City, CA (US)

(72) Inventor: Kapil Jain, Santa Clara, CA (US)

(73) Assignee: EmbodyVR, Inc., San Mateo, CA (US)

(*) Notice: Subject to any disclaimer, the term of this patent is extended or adjusted under 35 U.S.C. 154(b) by 31 days.

(21) Appl. No.: 15/811,392

(22) Filed: Nov. 13, 2017

(65) Prior Publication Data

US 2018/0139533 A1 May 17, 2018

Related U.S. Application Data

(60) Provisional application No. 62/421,285, filed on Nov. 13, 2016, provisional application No. 62/421,380, (Continued)

(51) Int. Cl.
*H04R 11/02* (2006.01)
*H04S 7/00* (2006.01)
(Continued)

(52) U.S. Cl.
CPC .............. *H04S 7/304* (2013.01); *A61B 5/121* (2013.01); *G01B 7/14* (2013.01); *G06K 9/00362* (2013.01); *G06K 9/66* (2013.01); *G06T 1/0007* (2013.01); *G06T 7/73* (2017.01); *G06T 7/80* (2017.01); *H04R 1/005* (2013.01); *H04R 1/1008* (2013.01); *H04R 1/1058* (2013.01); *H04R 1/22* (2013.01); *H04R 1/32* (2013.01); *H04R 1/323* (2013.01); (Continued)

(58) Field of Classification Search
CPC ........ A61B 6/2517; G06T 7/80; H04R 1/005; H04R 1/32; H04R 1/323; H04R 1/1008; H04R 5/033; H04R 11/02; H04S 7/301; H04S 7/304; H04S 7/306; H04S 2400/11; H04S 2420/01
See application file for complete search history.

(56) References Cited

U.S. PATENT DOCUMENTS

| 5,708,725 A | 1/1998 | Ito |
| 9,030,545 B2 | 5/2015 | Pedersen |

(Continued)

FOREIGN PATENT DOCUMENTS

| JP | 3521900 B2 | 4/2004 |
| KR | 20150009384 A | 1/2015 |
| WO | 2017047309 A1 | 3/2017 |

OTHER PUBLICATIONS

International Application Serial No. PCT/2017/061413, International Search Report dated Mar. 5, 2018, 3 pages.
(Continued)

*Primary Examiner* — Brian Ensey

(57) ABSTRACT

A signal indicative of sound detected by at least one sensor at an audio device is received. The audio device may at least partially covers a pinna and the detected sound may interact with at least a torso of a human body, but can also interact with the head and shoulder. The signal is modulated with a non-linear transfer function to generate a modulated signal indicative of one or more audio cues for spatializing the detected sound while the audio device at least partially covers a pinna. Sound is output by the audio device based on the modulated signal.

17 Claims, 13 Drawing Sheets

Related U.S. Application Data filed on Nov. 14, 2016, provisional application No. 62/424,512, filed on Nov. 20, 2016, provisional application No. 62/466,268, filed on Mar. 2, 2017, provisional application No. 62/468,933, filed on Mar. 8, 2017.

(51) Int. Cl.

| | | |
|---|---|---|
| *G01B 7/14* | (2006.01) | |
| *H04R 5/04* | (2006.01) | |
| *H04S 3/00* | (2006.01) | |
| *G06T 7/80* | (2017.01) | |
| *G06T 7/73* | (2017.01) | |
| *G06K 9/66* | (2006.01) | |
| *G06T 1/00* | (2006.01) | |
| *H04R 1/00* | (2006.01) | |
| *H04R 1/32* | (2006.01) | |
| *H04R 1/10* | (2006.01) | |
| *H04R 3/04* | (2006.01) | |
| *A61B 5/12* | (2006.01) | |
| *H04R 1/22* | (2006.01) | |
| *G06K 9/00* | (2006.01) | |
| *H04R 5/033* | (2006.01) | |
| *A61B 5/00* | (2006.01) | |
| *A61B 6/00* | (2006.01) | |

(52) U.S. Cl.
CPC ............... *H04R 3/04* (2013.01); *H04R 5/04* (2013.01); *H04S 3/008* (2013.01); *H04S 7/301* (2013.01); *H04S 7/306* (2013.01); *A61B 5/4005* (2013.01); *A61B 6/5217* (2013.01); *H04R 1/1016* (2013.01); *H04R 5/033* (2013.01); *H04R 11/02* (2013.01); *H04R 2201/029* (2013.01); *H04R 2225/77* (2013.01); *H04S 2400/11* (2013.01); *H04S 2420/01* (2013.01)

(56) References Cited

U.S. PATENT DOCUMENTS

| | | | |
|---|---|---|---|
| 9,473,858 B2 * | 10/2016 | Pedersen | H04R 25/407 |
| 9,544,706 B1 | 1/2017 | Hirst | |
| 9,900,722 B2 * | 2/2018 | Bilinski | H04S 7/302 |
| 10,181,328 B2 * | 1/2019 | Jensen | H04R 5/033 |
| 10,200,806 B2 * | 2/2019 | Stein | H04S 7/304 |
| 2003/0035551 A1 | 2/2003 | Light et al. | |
| 2004/0136538 A1 | 7/2004 | Cohen et al. | |
| 2006/0067548 A1 | 3/2006 | Slaney et al. | |
| 2006/0274901 A1 | 12/2006 | Terai et al. | |
| 2008/0107287 A1 | 5/2008 | Beard | |
| 2008/0175406 A1 | 7/2008 | Smith | |
| 2010/0215198 A1 | 8/2010 | Ngia et al. | |
| 2011/0009771 A1 | 1/2011 | Guillon et al. | |
| 2011/0206217 A1 | 8/2011 | Weis | |
| 2012/0183161 A1 | 7/2012 | Agevik et al. | |
| 2012/0328107 A1 | 12/2012 | Nystrom et al. | |
| 2013/0177166 A1 | 7/2013 | Agevik et al. | |
| 2013/0279724 A1 | 10/2013 | Stafford et al. | |
| 2014/0161412 A1 | 6/2014 | Chase et al. | |
| 2014/0270200 A1 | 9/2014 | Usher et al. | |
| 2015/0010160 A1 | 1/2015 | Udesen | |
| 2015/0172814 A1 | 6/2015 | Usher et al. | |
| 2016/0269849 A1 | 9/2016 | Riggs et al. | |
| 2017/0020382 A1 | 1/2017 | Sezan et al. | |
| 2017/0332186 A1 | 11/2017 | Riggs et al. | |
| 2018/0063652 A1 | 3/2018 | Perkins et al. | |

OTHER PUBLICATIONS

International Application Serial No. PCT/US2017/061417, International Search Report dated Mar. 5, 2018, 3 pages.

U.S. Appl. No. 15/811,642, Non-Final Office Action dated Mar. 15, 2018, 5 pages.

International Application Serial No. PCT/2017/061413, Written Opinion dated Mar. 5, 2018, 5 pages.

U.S. Appl. No. 15/811,386, Notice of Allowance dated Feb. 5, 2018, 7 pages.

International Application Serial No. PCT/2017/061417, Written Opinion dated Mar. 5, 2018, 8 pages.

Spagnol, et al., "Synthetic Individual Binaural Audio Delivery by Pinna Image Processing", International Journal of Pervasive Computing and Communications vol. 10 No. 3, 2014, pp. 239-254, Emerald Group Publishing Limited.

PCT Application Serial No. PCT/2018/052312, International Search Report dated Jan. 21, 2019, 3 pages.

International Application Serial No. PCT/2018/052312, Written Opinion dated Jan. 21, 2019, 7 pages.

\* cited by examiner

SPATIALLY AMBIENT AWARE PERSONAL AUDIO DELIVERY DEVICE

RELATED DISCLOSURES

This disclosure claims the benefit of priority under 35 U.S.C. § 119(e) of U.S. Provisional Application No. 62/421,380 filed Nov. 14, 2016 entitled "Spatially Ambient Aware Audio Headset", U.S. Provisional Application No. 62/424,512 filed Nov. 20, 2016 entitled "Head Anatomy Measurement and HRTF Personalization", U.S. Provisional Application No. 62/468,933 filed Mar. 8, 2017 entitled "System and Method to Capture and Characterize Human Auditory Anatomy Using Mobile Device, U.S. Provisional Application No. 62/421,285 filed Nov. 13, 2016 entitled "Personalized Audio Reproduction System and Method", and U.S. Provisional Application No. 62/466,268 filed Mar. 2, 2017 entitled "Method and Protocol for Human Auditory Anatomy Characterization in Real Time", the contents each of which are herein incorporated by reference in their entireties.

This disclosure is also related to U.S. application Ser. No. 15/811,386, filed Nov. 13, 2017, entitled "Method, System and Apparatus for Measuring Head Size Using a Magnetic Sensor Mounted on a Personal Audio Delivery Device" US application Ser. No. 15/811,295, filed Nov. 13, 2017, entitled "Image Audio Based Characterization of a Human Auditory System for Personalized Audio Reproduction", U.S. application Ser. No. 15/311,642, filed Nov. 13, 2017, entitled "Audio Based Characterization of a Human Auditory System for Personalized Audio Reproduction", and U.S. application Ser. No. 15/811,441, filed Nov. 13, 2017, entitled "System and Method to Capture Image of Pinna and Characterize Human Auditory Anatomy using Image of Pinna", the contents each of which are herein incorporated by reference in their entireties.

FIELD OF THE DISCLOSURE

The disclosure is related to consumer goods and, more particularly, to a personal audio delivery device which facilitates spatial localization of sounds. The spatial localization is facilitated by providing audio cues indicative of a direction where the sounds are coming from to a person wearing the personal audio delivery device.

BACKGROUND

A human auditory system includes an outer ear, middle ear, and inner ear. With the outer ear, middle ear, and inner ear, the human auditory system is able to hear sound. For example, a sound source such as a loudspeaker in a room may output sound. A pinna of the outer ear receives the sound, directs the sound to an ear canal of the outer ear, which in turn directs the sound to the middle ear. The middle ear of the human auditory system transfers the sound into fluids of an inner ear for conversion into nerve impulses. A brain then interprets the nerve impulses to hear the sound. Further, the human auditory system is able to perceive the direction where the sound is coming from. The perception of direction of the sound source is based on interactions with human anatomy. The interaction includes the sound reflecting and/or reverberating and diffracting off a head, shoulder and pinna. The interaction generates audio cues which are decoded by the brain to perceive the direction where the sound is coming from.

It is now becoming more common to listen to sounds wearing personalized audio delivery devices such as headphones, hearables, earbuds, speakers, or hearing aids. The personalized audio delivery devices outputs sound, e.g., music, into the ear canal of the outer ear. For example, a user wears an earcup seated on the pinna which outputs the sound into the ear canal. Alternatively, a bone conduction headset vibrates middle ear bones to conduct the sound to the human auditory system. The personalized audio delivery devices accurately reproduce sound. But unlike sound from a sound source, the sound from the personalized audio delivery devices does not interact with the human anatomy such that direction where the sound is coming from is accurately perceptible. The seating of the earcup on the pinna prevents the sound from the personal audio delivery device from interacting with the pinna and the bone conduction may bypass the pinna altogether. Audio cues indicative of direction is not generated and as a result the person is not able to perceive the direction where the sound is coming from.

BRIEF DESCRIPTION OF THE DRAWINGS

Features, aspects, and advantages of the presently disclosed technology may be better understood with regard to the following description, appended claims, and accompanying drawings where:

Figure 1:
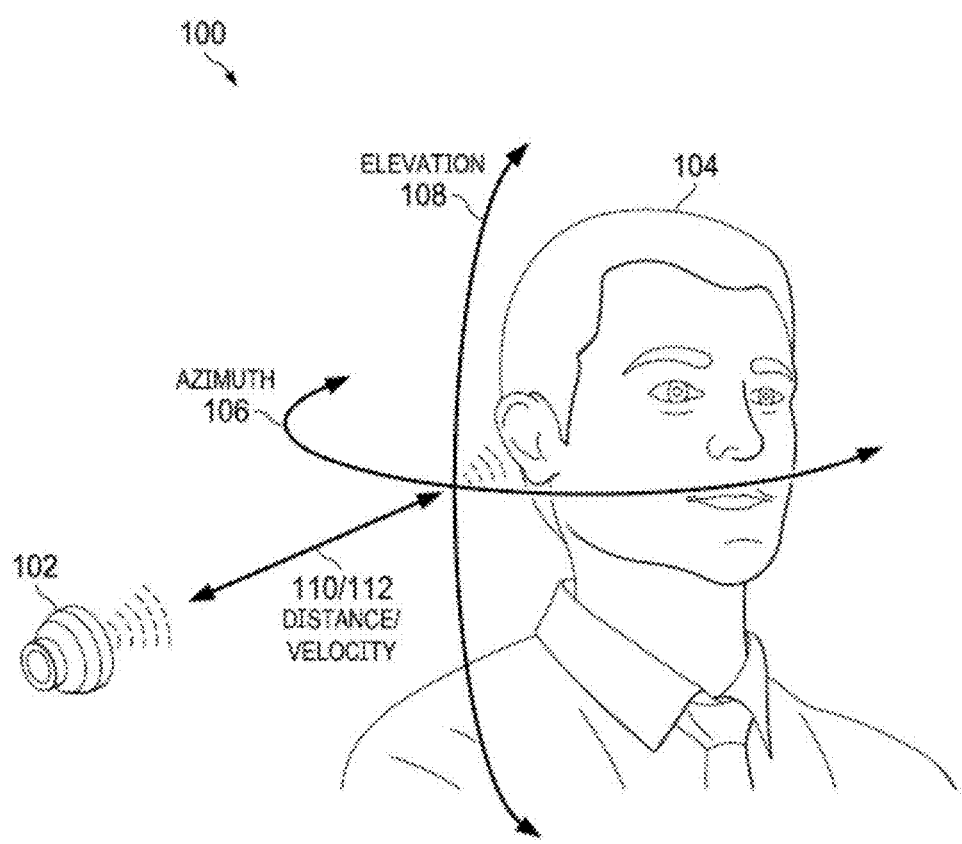
FIG. 1 is an example visualization of various parameters used for spatial localization of sound.

The drawings are for the purpose of illustrating example embodiments, but it is understood that the embodiments are not limited to the arrangements and instrumentality shown in the drawings.

DETAILED DESCRIPTION

A sound source may output sound. A direction where the sound comes from may be identified by the human auditory system using one or more audio cues. The audio cues may be sound (e.g., reflections and reverberations) indicative of a spatial location of the sound, e.g., where the sound is coming from. The audio cues may be generated from interactions between the sound, objects in an environment, and human anatomy before reaching the human auditory system. For example, reverberation and reflection from the objects may generate audio cues. Additionally, or alternatively, aspects of the human anatomy such as head shape, head size, shoulder shape, shoulder size, and outer ear (pinna) structure may generate audio cues. Each person may have different human anatomy. In this regard, the audio cues used by one person to spatially localize the sound may be different for another person.

FIG. 1 is an example visualization 100 of parameters which facilitates spatially localizing sound output by a sound source 102. One or more parameters may describe a relationship between a position of a listener 104 and the sound source 102. The parameters may include an azimuth 106, elevation 108, and a distance and/or velocity 110/112. The azimuth 106 may be an angle in a horizontal plane between the listener 104 and the sound source 102. The elevation 108 may be an angle in a vertical plane between the listener 104 and the sound source 102. The distance 110 may be a separation between the listener 104 and the sound source 102. The velocity 112 may describe a rate of movement of the sound source 102. Other parameters indicative of direction may also be used.

Figure 2:
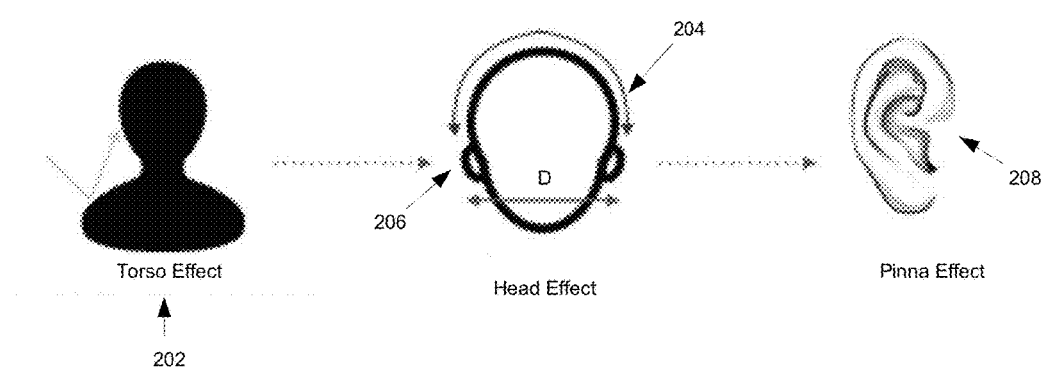
FIG. 2 shows aspects of a human anatomy in spatial localization of sound.

FIG. 2 shows aspects of a human anatomy 202-208 used in sound localization. Audio cues may be generated based on the interaction of sound with the human anatomy. The audio cues may be indicative of a spatial location from where sound comes from. The human anatomy which is illustrated includes a torso 202, head 204 with ears 206, and pinna 208.

Reflections of sound from the torso 202 may generate an audio cue indicative of one or more of an elevation and distance from where the sound is coming from. These reflections are modeled as torso effect. Overall shape of the head 204 including ear symmetry and distance D between the ears 206 may generate an audio cue regarding one or more of an azimuth and elevation from where the sound is coming from. This is modeled as head effect. Finally, how sound interacts with the shape, size, and structure of the pinna 208 may generate an audio cue regarding one or more of an elevation, azimuth, distance and velocity from where the sound comes from.

Figure 3:
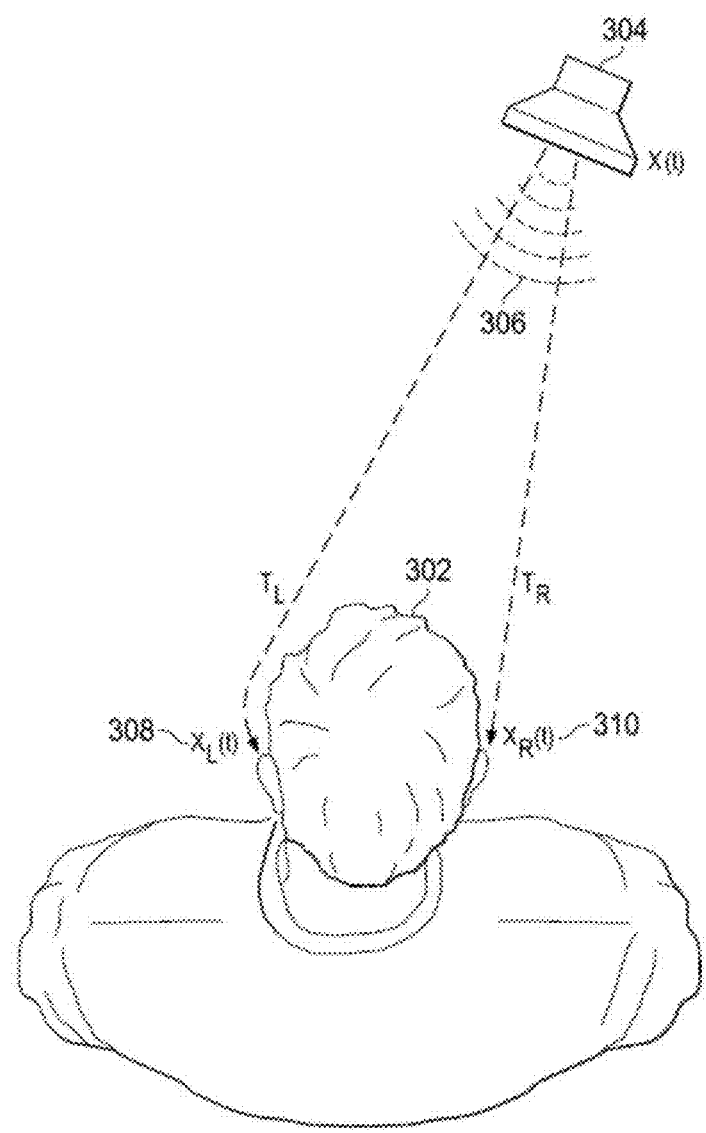
FIG. 3 shows an example of an effect of human anatomy on interaural audio cues.

FIG. 3 shows how the audio cue indicative of azimuth is generated. A person 302 may be located a certain distance away from a sound source 304. The sound source 304 may output sound 306 which is then perceived by the person at a left ear 308 and a right ear 310.

An interaural time difference (ITD) represents a difference in time arrival between the two ears 308, 310. Sound generated by sound source 304, x(t), takes $T_L$ amount of time to reach the left ear 308 and $T_R$ amount of time to reach the right ear 310. ITD represents difference between $T_L$ and $T_R$. Similarly, at any time t, sound pressure level at left ear 308 $X_L(t)$ is different from the one experienced at right ear 310 $X_R(t)$. This difference in intensity is represented by an interaural level difference (ILD) audio cue. These audio cues (ITD and ILD) may be different for a different shape and size of head. A bigger head i.e. larger distance between left and right ear 308, 310, will generate larger time and intensity difference than a smaller head.

The ITD and ILD audio cues may be directly proportional to the azimuth between the listener and the sound source. In this regard, azimuth of the sound source may be perceived. ITD and ILD, however, may be insufficient to further localize the direction of the sound in terms of elevation, distance and velocity.

Figure 4:
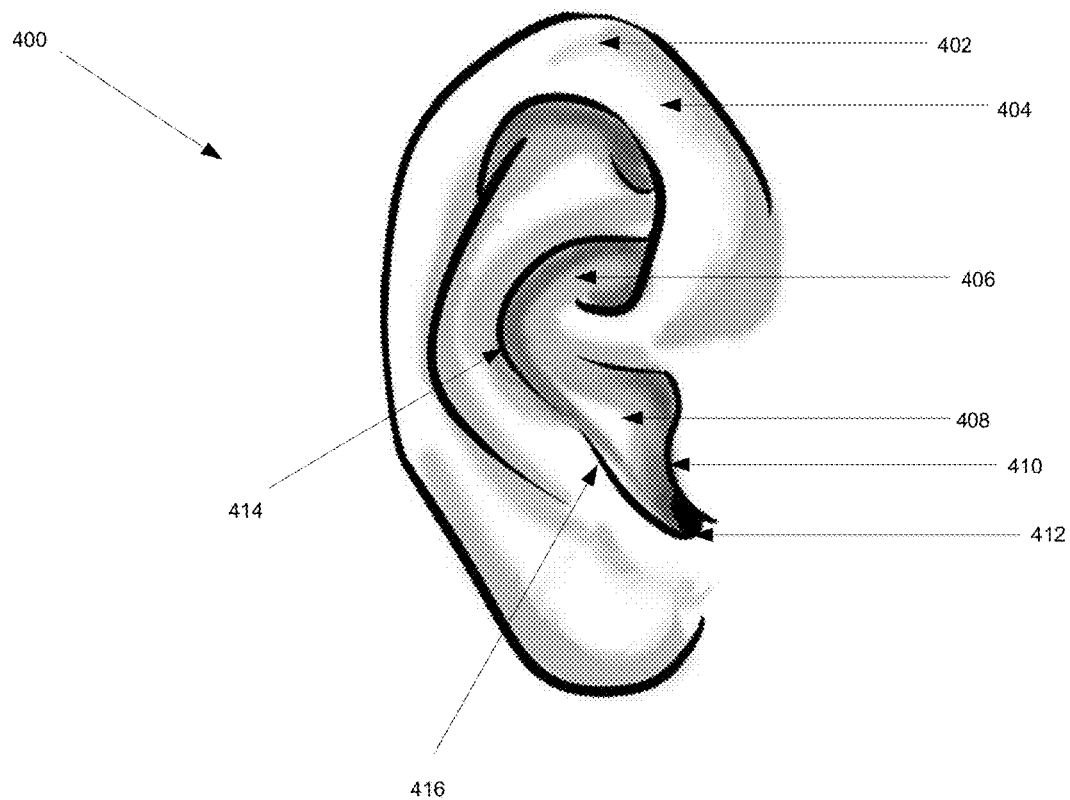
FIG. 4 shows a detailed view of a pinna of the human anatomy.

FIG. 4 shows a detailed view of an anatomy of a pinna 400 and how the sound may be transformed. The pinna 400 may have various features. The features may include a height, width, shape, and depth of the pinna 400. Additionally, the features may include a helix 402, fossa 404, cymba conchae 406, cavum conche 408, tragus 410, ear notch 412, antihelix 414, and antitragus 416 among other features. The features form one or more cavities within which sound may resonate and/or reflect. For example, an amplitude of sound from a sound source may be increased at certain frequencies and decreased at other frequencies due to the structure of the pinna. The increase and/or decrease may be due to the reflection and/or reverberations associated with features of the pinna 400. The transformation of the sound may generate audio cues. In turn, these audio cues may be used to further localize the direction of sound in terms of the elevation, distance, and velocity.

Personal audio delivery devices such as headphones, earbuds, earphones, speakers, hearables, and hearing aids may output sound directly into the human auditory system. For example, an earcup of a headphone may be placed on the pinna and a transducer in the earcup may output sound into an ear canal of the human auditory system. However, the earcup may cover or partially cover the pinna. In another example, an earbud may not have an earcup but still output sound into an ear canal of the human auditory system while partially covering the pinna. As a result, the pinna might not interact with such sound so as to generate audio cues to perceive the direction where the sound is coming from.

Embodiments described herein are directed to a personal audio delivery device arranged to provide spatial localization to real-world sound heard by a person wearing the personal audio delivery device. Real-world sound may be sound output by sources other than the personal audio delivery device. The person would not otherwise be able to accurately spatial localize the real-world sound, e.g., determine where the sound is coming from, because wearing of the personal audio delivery device prevents the real-world sounds from interacting with the pinna to generate audio cues indicative of the spatial location. Spatial localization of sound has many benefits especially in sports such as running and cycling where a person may be listening to music while engaging in the sports. For instance, a person running or cycling on roadways can also be spatially aware of sounds around him such as car horns and emergency sirens on the roadways so that he can correct his behavior based on the direction the sounds are coming from to remain safe. Spatial localization of sound as other benefits as well.

In examples, audio cues to facilitate spatial localization may be artificially generated based on a non-linear transfer function, e.g., also referred to as a head related transfer function (HRTF) or transfer function (which could be linear or non-linear), may facilitate generating the audio cues. The non-linear transfer function may characterize how sound is received by a human auditory system based on interaction with the head, torso, shoulder, pinna and other parts of the human anatomy influencing human auditory localization. The non-linear transfer function may be used to artificially generate the audio cues for determining azimuth, elevation, distance and/or velocity of a sound source.

Figure 5A:
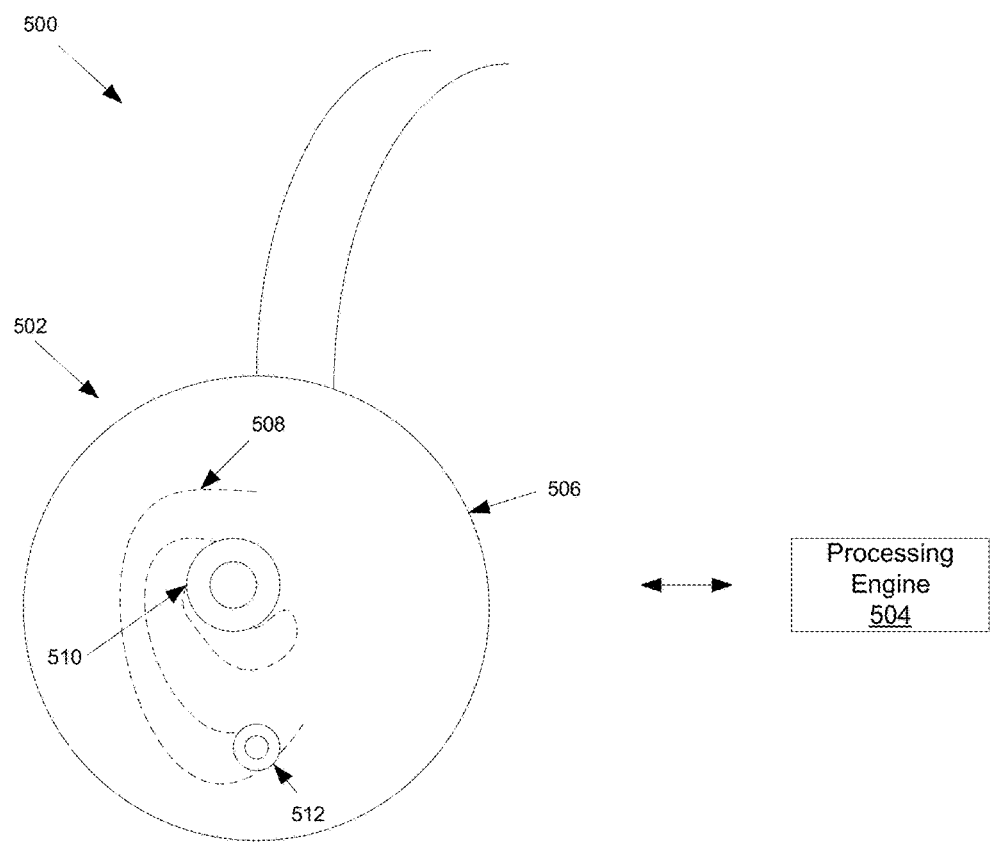
FIGS. 5A and 5B show an example system for spatial localization of sound.

FIG. 5A illustrates an example system 500 for spatial localization. The system 500 may include the personal audio delivery device 502 such as a headset which outputs sound such as voice or music and a processing engine 504.

The personal audio delivery device 502 may have an earcup 506 which is worn on a pinna 508. The pinna 508 may not be visible externally when the earcup 506 is worn, but pinna 508 is shown as visible for purposes of illustration. The earcup 506 may have one or more transducers 510 and one or more sensors 512. The transducer 510 may be a speaker which outputs audible sound based on conversion of an electrical signal representative of the sound. The sensor 512 may take the form of a microphone which detects audible sound and converts the audible sound into an electrical signal.

The personal audio delivery device 502 may be used in an environment where sounds may be generated by sound sources other than by the personal audio delivery device 502. These sounds are referred to as real-world sounds. For example, the sound source may be a car horn, emergency vehicle sound, other people etc., in contrast to music output by the transducer 510 of the personal audio delivery device 502. The sensor 512 may detect this sound and convert the sound to an electrical signal. In some cases, the sensor 512 on the earcup 502 may be mounted so that it faces away from the pinna 508 and/or transducer 510 to improve the sampling of the real-world sound as compared to the sound output by the transducer 510. The processing engine 504 may process the signal associated with the sensor and/or transducer.

Figure 5B:
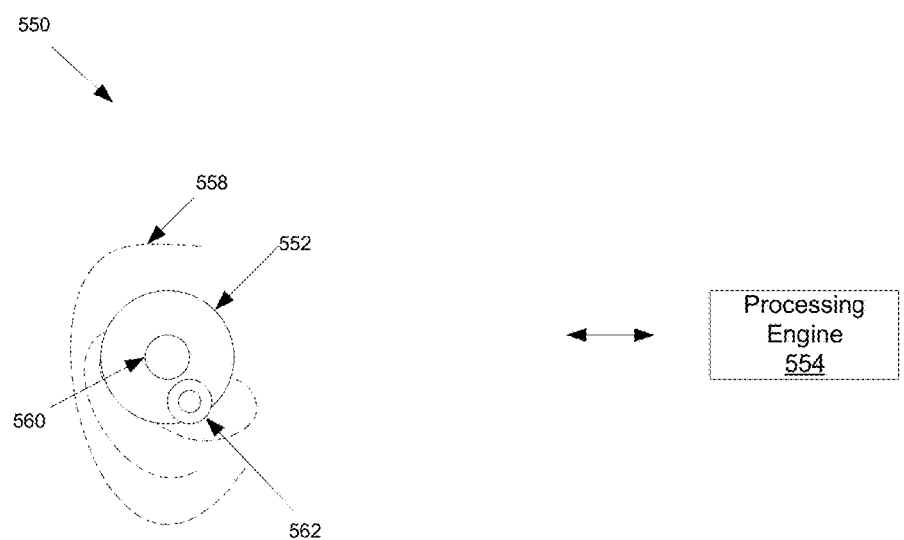

FIG. 5B illustrates another example system 550 for spatial localization. The system 550 may include the personal audio delivery device such as an earbud 552 which outputs sound such as voice or music into the ear canal and a processing engine 554. Unlike the personal audio delivery device 502, the earbud 552 may be held in place on the pinna 558 by being inserting into the ear canal. As a result, the earbud 552 may cover less of the pinna 558 compared to the earcup 506. The example system 550 may also include the processing engine 554, transducer 560, and sensor 562.

In general, the personal audio delivery device (also referred to as audio delivery device) may take a variety of forms. The personal audio delivery device may be a headset or earbud as described above. Alternatively, the personal audio delivery device may be hearables or hearing aids Other variations are also possible and the disclosed spatialization is not limited by the form by which the personal audio delivery device takes.

Figure 6A:
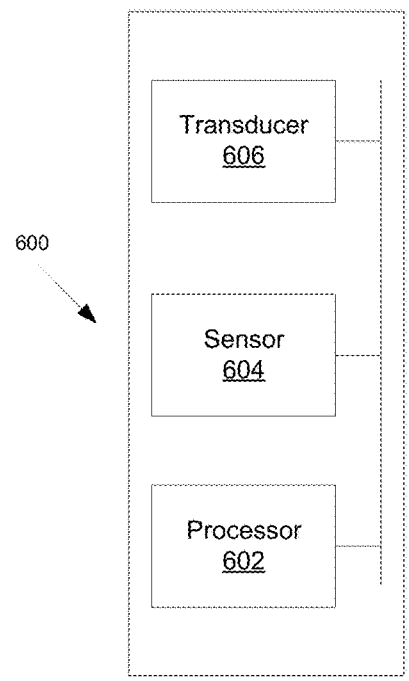
FIGS. 6A and 6B show example arrangements of a processing engine in the example system for spatial localization of sound.
Figure 6B:
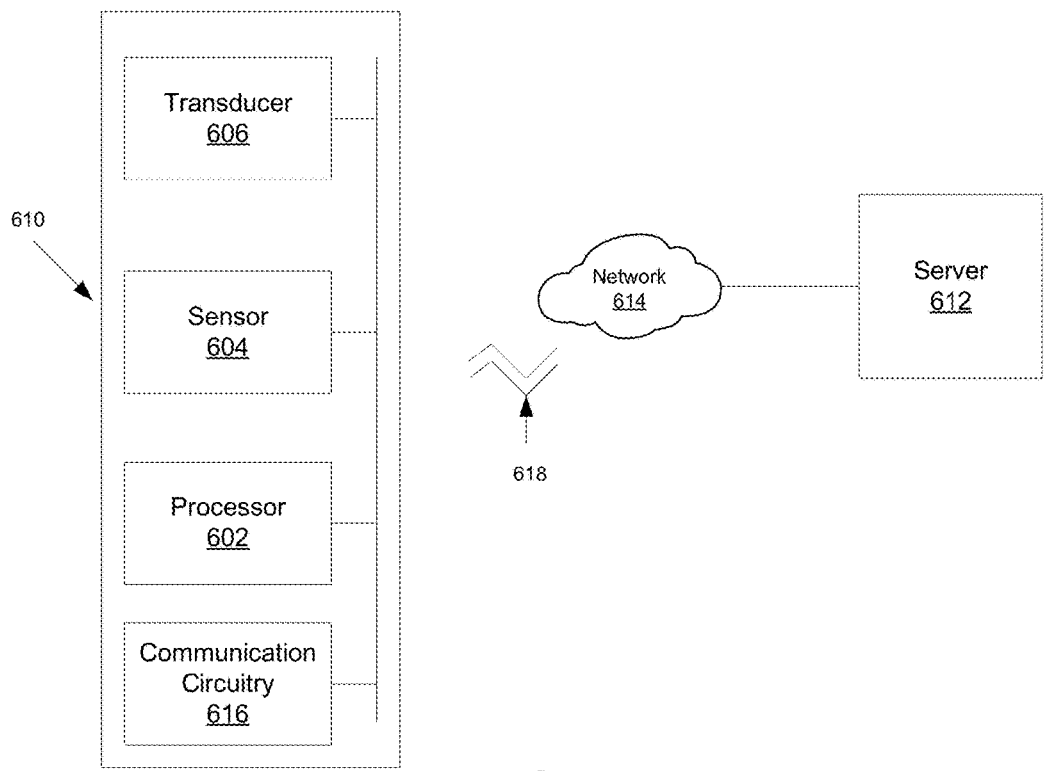

FIGS. 6A and 6B show example arrangements of the processing engine 504 in the example system for spatial localization. The processing engine may take the form of a processor or a server, among other arrangements.

FIG. 6A shows an arrangement of a personal audio delivery device 600 with a processing engine in the form of the processor 602. The processor 602 may be a central processing unit (CPU) local to the personal audio delivery device 600 which executes computer instructions stored in storage such as memory to process the signals associated with the one or more sensors 604 and one or more transducers 606. The processor 602 may be local when the processor 602 is integrated with the personal audio delivery device 600.

FIG. 6B shows an arrangement of a personal audio delivery device 610 and a processing engine in the form of a server 612 coupled via a network 614. The server 612 may be a network based computing system. The server 612 may process the signals associated with the one or more sensors 604 and one or more transducers 606. The server 612 may be accessible to the personal audio delivery device via the network 614. The network 614 may take the form of a wired or wireless network. The personal audio delivery device 612 may have communication circuitry 616 for communicating signals 618 with the server 612, e.g., via WiFi or Ethernet, to facilitate processing of signals associated with the transducers and/or sensors.

Latency associated with processing the signals associated with the sound output by the one or more transducers and/or sound detected by the one or more microphones by the local processor may be less compared to the server. The latency may be less because there is no delay associated with communication to the server. The personal audio delivery device may be powered by a battery. Processing signals on the local processor may reduce how long a personal audio delivery device may operate before the battery source needs to be charged or replaced. The processing of the signals associated with the sound output by the one or more transducers and/or one or more microphone may consume power from the battery which otherwise would be used by the personal audio delivery device to output sound.

The processing engine may take other forms as well. For example, the processing engine may take the form of the CPU local to the personal audio delivery device and the server. In other words, the processing of the signals may be performed locally by the processor at the personal audio delivery device as well as remotely at the server. Yet other variations are also possible.

Figure 7:
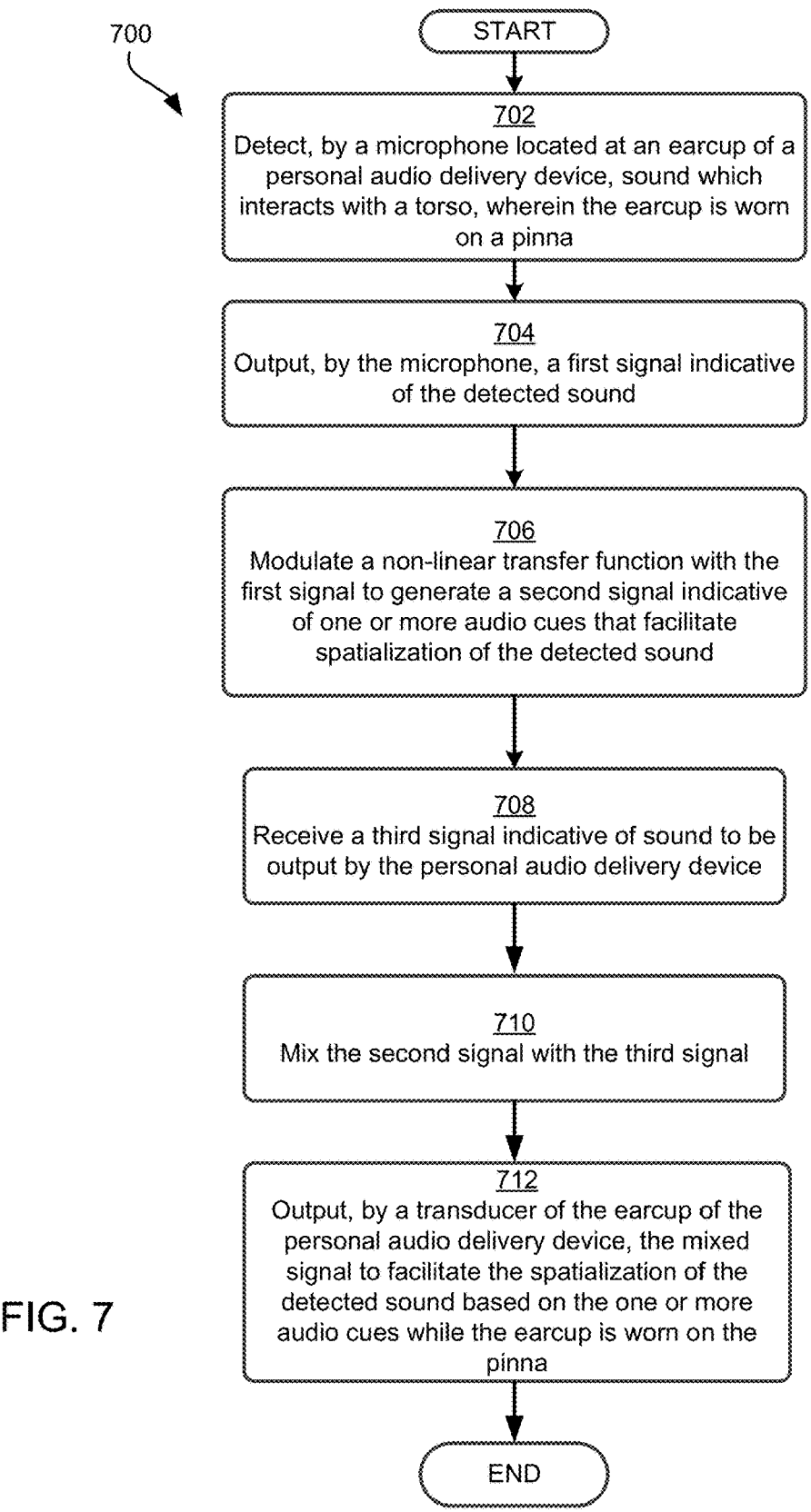
FIG. 7 is an example flow chart of functions with providing spatial localization of real-world sound heard by a person wearing a personal audio delivery device.

FIG. 7 is a flow chart 700 of functions associated with providing spatial localization to real-world sounds beard by a person wearing the personal audio delivery device. These functions may be performed by the example system 500 which includes the personal audio delivery device and processing engine.

Briefly, at 702, sound which interacts with certain human anatomy, e.g., torso, head, and/or shoulder, is detected by a microphone located at an earcup. The earcup may be worn on a pinna and the sound may be real-world sound which interacts with the torso. At 704, a first signal indicative of the detected sound is output by the microphone. At 706, a non-linear transfer function is modulated with the first signal to generate a second signal indicative of one or more audio cues that facilitate spatialization of the detected sound. At 708, a third signal is received indicative of sound to be output by the personal audio delivery device. At 710, the second signal may be mixed with the third signal. At 712, the mixed signal is output by a transducer of the earcup of the personal audio delivery device to facilitate the spatialization of the detected sound based on the one or more audio cues while the earcup is worn on the pinna.

Methods and the other process disclosed herein may include one or more operations, functions, or actions. Although the blocks are illustrated in sequential order, these blocks may also be performed in parallel, and/or in a different order than those described herein. Also, the various blocks may be combined into fewer blocks, divided into additional blocks, and/or removed based upon the desired implementation.

In addition, for the methods and other processes and methods disclosed herein, the flowchart shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device. In addition, each block in the FIGS. may represent circuitry that is wired to perform the specific logical functions in the process.

An individual may wear a personal audio delivery device. The personal audio delivery device may have an earcup which the individual wears on a pinna. Referring back, at 702, sound is detected by a microphone located at the earcup worn on the pinna. The microphone may detect the sound by digitally sampling the sound using a sample and hold circuit or other analog to digital conversion circuit. The sound that is detected may be real-world sound which interacts with certain human anatomy, e.g., a torso, head, and/or shoulder, of a person wearing the earcup. The real-world sound may be sound output not sound output by the transducer. In some examples, the microphone may be directed away from the pinna on which the earcup is worn to facilitate detecting the real-world sound as opposed to any sound being output by a transducer located at the earcup.

At 704, the microphone may output a first signal indicative of the detected sound. The first signal may define one or more samples of the detected sound. The first signal may be provided to the processing engine. Additionally, or alternatively, the microphone may output an indication of a direction from where the detected sound comes from. For example, the microphone may be a directional microphone which picks up sound coming from a certain direction. As another example, the microphone may be an array of microphones. Each microphone in the array may be oriented in a certain direction. If certain microphones pick up more sound than other microphones, then the orientation of those microphones which pick up more sound may be indicative of the direction of the sound. The determination of direction based on the array of microphones is commonly known as beamforming. The microphone may output an indication of the direction and/or the direction may be determined based on a microphone output.

In the event that the personal audio delivery device has two earcups, then respective microphones associated with each earcup may sample the real-world sound. A left microphone may sample sound near a left pinna and a right microphone may sample sound near a right pinna. In one example, the sampling may occur independently such that each microphone may output a respective signal which is processed in accordance steps 704-712. Additionally, the plurality of microphones which receive the sound may be used to determine a direction from where the sound comes from, e.g., via beamforming, which is then used to apply a non-linear transfer function based on the direction to the sampled sound associated with the left and right microphones. In another example, the respective signals output by each microphone may be combined together and this combined signal may be processed in accordance steps 704-712. Other variations are also possible.

The real-world sound may interact with certain human anatomy, e.g., a torso, head, and/or shoulder. However, the real-world sound may not properly interact with the pinna because the earcup of the personal audio delivery device may cover or partially cover the pinna. As a result, audio cues associated with pinna may not be generated to facilitate determining a direction where the real-world sound comes from.

At 706, a non-linear transfer function is modulated with the first signal. In some examples, the non-linear transfer function may be an impulse response which is convolved with the first signal in a time domain or multiplied with the first signal in a frequency domain. The modulation may result in adjusting the first signal based on this non-linear transfer function to form a modulated signal.

The non-linear transfer function may characterize how sound is transformed by the pinna. Because the real-world sound does not interact with the pinna, audio cues associated with spatial location of the sound may be missing. The modulation of the first signal with the non-linear transfer may result in artificially generating these missing audio cues. In particular, audio cues for determining elevation, azimuth, distance and/or velocity of the sound source may be generated. These audio cues can be used to facilitate the spatial location of the real-world sound. Sounds from a car hoop emergency vehicle sirens, and people, for instance, can be spatialized improving safety of the user wearing the personal audio delivery device. In this regard, the modulated signal may be a second signal indicative of one or more audio cues that facilitate spatialization of the detected sound.

Figure 8:
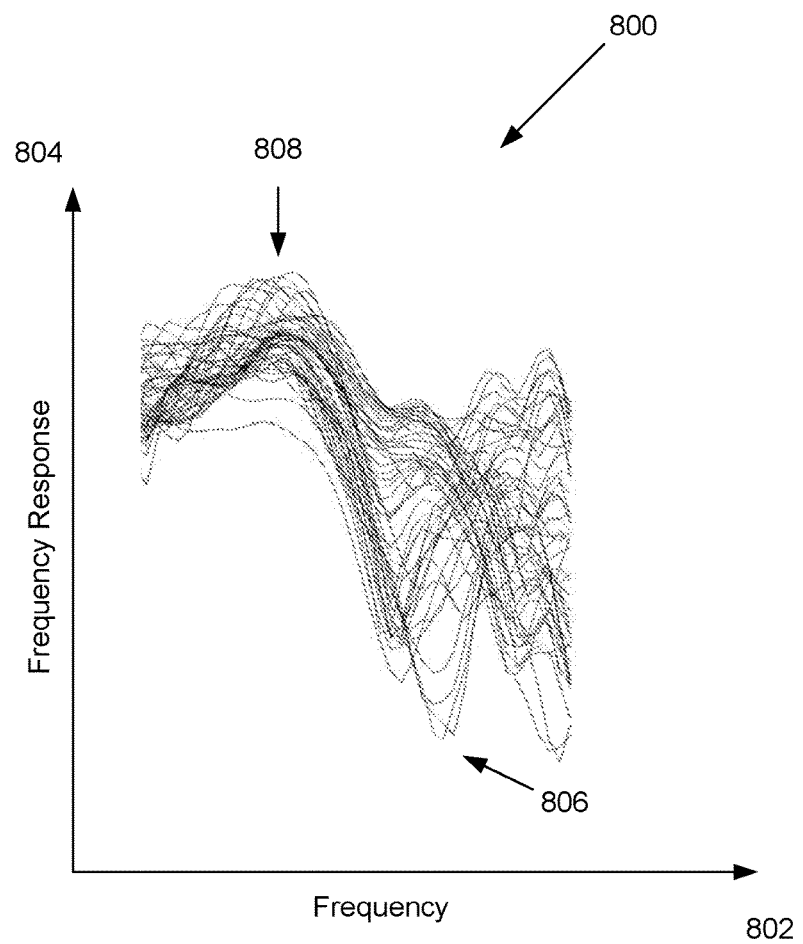
FIG. 8 shows an example of a non-linear transfer function associated with spatial localization of sound.

FIG. 8 shows an example of the non-linear transfer function 800 for generating the missing audio cues. A horizontal axis 802 may represent a frequency heard at a pinna, e.g., in Hz, while a vertical axis 804 may represent a frequency response, e.g., in dB. The non-linear transfer function may characterize how a pinna transforms sound. For example, the non-linear transfer function may define waveforms indicative of frequency responses of the pinna at different elevations of the sound, source. For example, each waveform may be associated with a particular elevation of the sound source. Further, each waveform may be associated with a same azimuth of a sound source. In this regard, a waveform for a given elevation may define the frequency response of the pinna when sound comes from the given elevation and azimuth. Further, regions 806 may represent notches and regions 808 may represent peaks in the frequency response of the pinna.

The non-linear transfer functions may take other forms as well. For example, the non-linear transfer function may describe one or more of a frequency response of the pinna versus elevation for a given azimuth and/or a frequency response of the pinna versus azimuth for a given elevation. In other cases, the non-linear transfer function may describe a frequency response with respect to a plurality of dimensions including distance, velocity, elevation, and/or azimuth.

The modulation process may be now described in more detail. The microphone which detects the sound at 702 may also detect a direction where the sound is coming from. The direction of the sound detected by the one or more microphones may be used in conjunction with the non-linear transfer function to spatialize the sound detected by the microphone. A frequency response of the non-linear transfer function associated with the direction may be modulated with a sound signal associated with the detected sound to generate one or more audio cues that facilitate spatialization of the detected sound. For example, the sound detected by the microphone may be coming from a given azimuth and elevation. The non-linear transfer function may define waveforms indicative of a frequency response of the pinna when sound comes from the given azimuth and elevation. These waveforms may be modulated with the sound signal to generate the second signal indicative of one or more audio cues. The audio cues may enable a user to perceive the detected sound coming from the given azimuth and elevation FIGS. 9A-E illustrate example arrangements associated with determining the non-linear transfer function. The non-linear transfer function may be determined in a variety of ways.

Figure 9A:
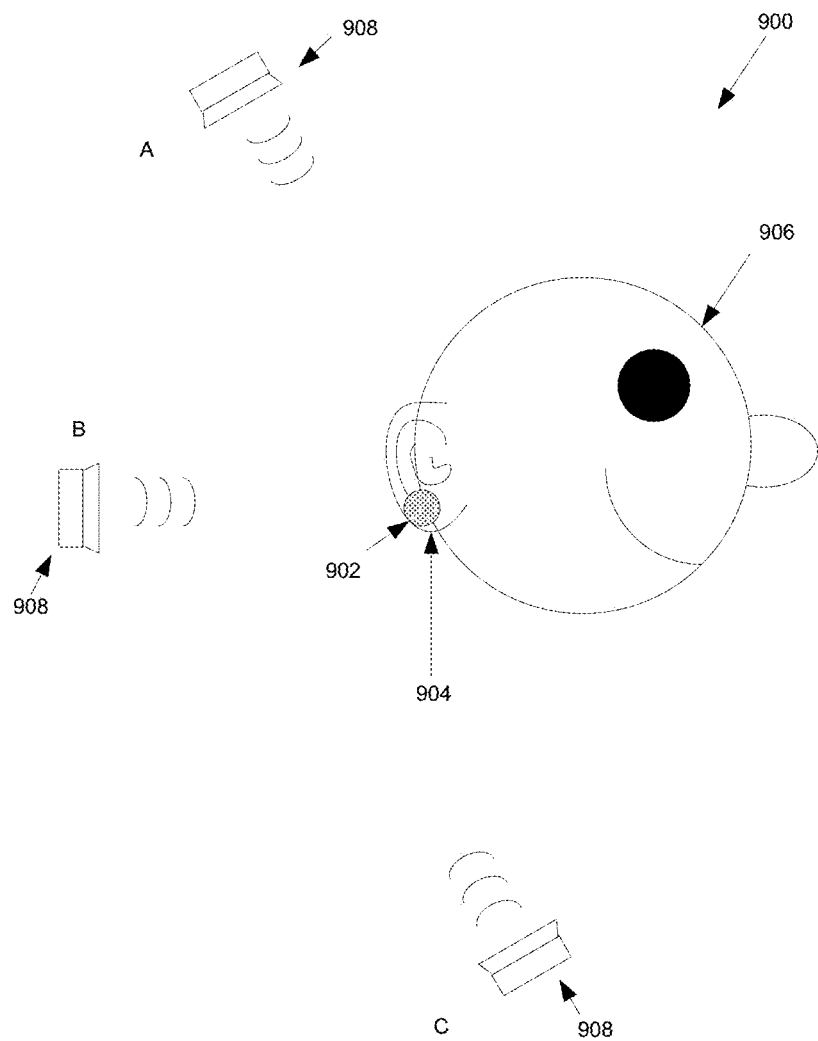
FIGS. 9A-E illustrate example arrangements associated with determining the non-linear transfer function.

FIG. 9A illustrates an example arrangement 900 associated with determining the non-linear transfer function via a direct measurement. A microphone 902 may be placed near an entrance of an ear canal 904 of an individual 906 for whom audio cues is to be generated at step 706. Then, a sound source 908 may be moved around the individual 906. The sound source 908 may be moved to a plurality of spatial locations in azimuth, elevation, distance, and/or velocity around the individual, examples which are shown as positions A, B, and C. At each location, the sound source 908 may output sound which may take the form of a chirp with varying frequency in an audible range of a human, i.e., 20 Hz to 20 kHz. Other sounds may also be used bandlimited between 20 Hz to 20 kHz such as an impulse. A frequency response of the pinna 904 measured by the microphone 902 in the pinna 904 for the plurality of spatial locations may be indicative of the non-linear transfer function. In some cases, a plurality of non-linear transfer functions may be determined. The plurality of non-linear transfer functions may describe one or more of a frequency response of the pinna versus elevation for a given azimuth, a frequency response of the pinna versus elevation for a given distance, and/or a frequency response of the pinna versus elevation for a given velocity, among others. This non-linear transfer function may be unique to the individual 906 such that a direct measurement performed for the pinna 902 of another individual would result in a different non-linear transfer function.

Alternatively, direct measurements may be performed during a learning process for a plurality of individuals different from the individual for whom audio cues is to be generated at 706. A direct measurement performed for a given individual of the plurality of individuals may result in determining a given non-linear transfer function. Additionally, in some examples, an image of a pinna may be determined for the given individual and associated with the given non-linear transfer function for the given individual. In this regard, the learning process may involve determining a plurality of non-linear transfer functions and/or associated images of a pinna.

Figure 9B:
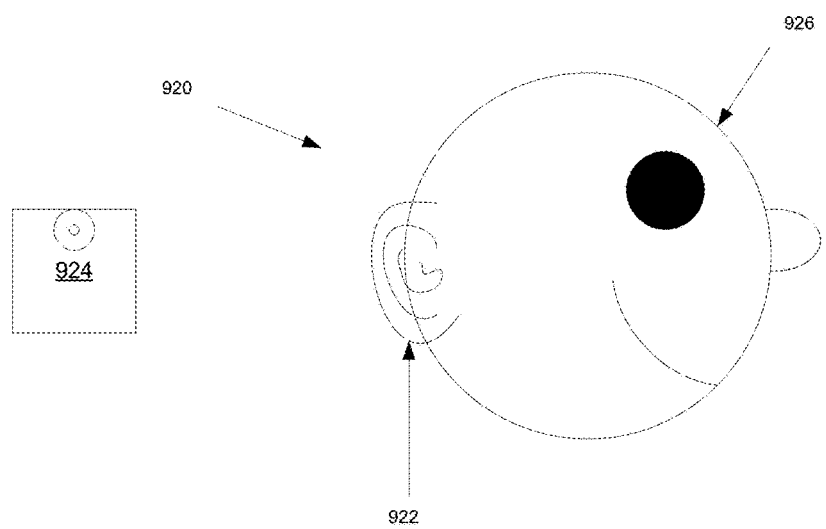

FIG. 9B illustrates an example arrangement 920 for determining the image of the pinna. The image of the pinna 922 may be captured by an imaging device 924 such as a camera or mobile phone for an individual 926 who is different from the individual for whom audio cues is to be generated at 706.

Figure 9D:
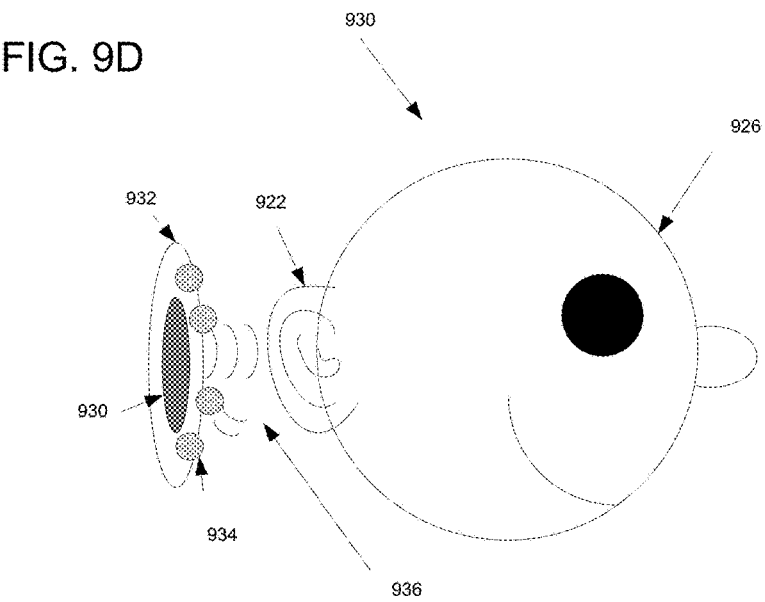
Figure 9C:
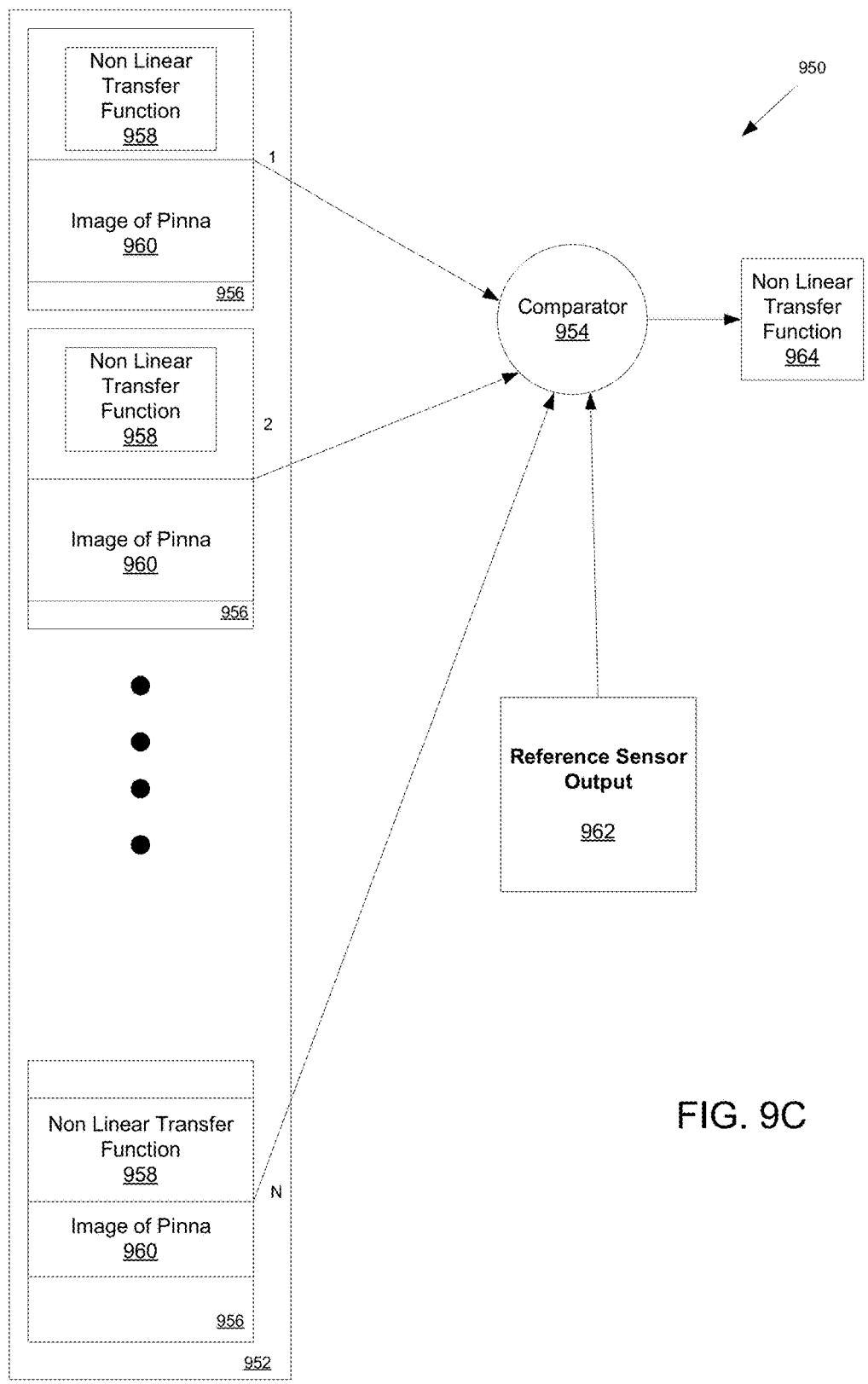

FIG. 9C illustrates an example arrangement 950 for determining the non-linear transfer function for the individual for whom audio cues is to be generated at 706 without having to perform a direct measurement as shown in FIG. 9A for the individual.

The example arrangement 950 may include a database 952 and comparator 954. The database 952 and comparator 954 may reside on the personal audio delivery device, server, or some other device. The database 952 may store the plurality of non-linear transfer functions determined during the learning process. Additionally, in some examples, the database 952 may store images of the pinna associated with the plurality of non-linear transfer functions determined during the learning process. For example, an entry 956 in the database 952 may define a respective non-linear transfer function 958 and in those cases an image of the pinna 960 of the individual associated with the non-linear transfer function. The database may have a plurality of entries 1:N. The example arrangement may also include a reference sensor output 962. In some examples, a reference sensor output 962 may be indicative of one or more frequency responses of the pinna for the individual for whom the audio cues is to be generated.

FIG. 9D show an example of how the one or more frequency responses may be determined. An individual may wear a personal audio delivery device. The personal audio delivery device may have an earcup 932 which an individual 926 wears on a pinna 922. The earcup 932 may be in contact with the pinna 922, but for purposes of illustration the earcup 932 is not shown as such. The earcup 932 may have one or more transducers 930 for outputting audio sound and one or more microphones 934 located at specific locations around a pinna 922. For example, the earcup 932 may have four microphones 934 located at four specific features of the pinna, such as the fossa, cymba conchae, cavum conchae, and ear notch.

A signal indicative of first sound may be provided to the one or more transducers 930 to cause the one or more transducers 930. In the earcup 932 to output the first sound. The first sound may take a variety of forms, and in some cases, be similar to the sound used during the learning process. For example, the first sound may take the form of a chirp with varying frequency in an audible range of a human, i.e., 20 Hz to 20 kHz. Alternatively, the first sound may take the form of an impulse. Other sounds may also be used bandlimited between 20 Hz to 20 kHz.

As the first sound is output, the first sound reflects and resonates within features of the pinna creating audio scatter. Each microphone 934 of one or more microphones in the earcup 932 may detect respective second sound. The detected respective second sound for a microphone is the sound received by that microphone which may be different from the detected respective sound for another microphone. The detected respective second sound of each of the one or more microphones 934 may be indicative of a frequency response of a pinna on which the earcup is worn at the location of the microphone 934 caused by an interaction between the first audio sound and the pinna. The first sound output by the one or more transducers 930 may have been chosen so that the detected respective second sound of each of the one or more microphones 934 uniquely characterizes the pinna.

If the earcup has four microphones, then the reference sensor output 962 may include at least four detected respective second sound corresponding to the locations of the four microphones. The comparator 960 may be arranged to compare frequency responses associated with the respective non-linear transfer function 958 to the detected respective second sound by each of the one or more microphones 934 associated with the reference sensor output 962 to identify a non-linear transfer function 958 in the entries 1:N which is close (e.g., similar) to the reference sensor output 962. The closeness of match may be based on a distance between one or more of the frequency responses of the pinna associated with non-linear transfer function 958 and the detected respective second sound of each of the one or more microphones, among other measures. The comparator 954 may output a non-linear transfer function 964 associated with the closeness (e.g., a closest match).

In some examples, the reference sensor output 962 may be an image of the pinna for the individual for whom the audio cites is to be generated. The comparator 960 may be arranged to compare characteristics of the features of the pinna associated with the reference sensor output 962 to corresponding characteristics of one or more features of the pinna associated with an image of the pinna 960 associated with the non-linear transfer function 958 to identify the image of the pinna 958 which is close to the reference sensor output 962. Various image processing techniques may be used by the processing engine to determine the characteristics of the features of the pinna, including identifying a feature of the pinna, extracting the feature from the image, and then determining a characteristic of the feature. The characteristics may include, but not be limited to an overall size and shape of the pinna (e.g., length, width, radius), a size and shape (e.g., length, width, radius) of the helix, fossa, cymba conchae, cavum conche, tragus, ear notch, antihelix, and antitragus, among other features, and relative distance between the helix, fossa, cymba conchae, cavum conche, tragus, ear notch, antihelix, and/or antitragus among other features. The comparator 954 may output a non-linear transfer function 964 associated with an image of the pinna 960 which is close to the reference sensor output 962 (e.g., a closest match).

In yet another example, the detected respective second sound of each of the one or more microphones and the image of the pinna for the individual for whom the audio cues is to be generated may be used together to identify the non-linear transfer function 964. The comparator 954 may be arranged to compare the image of the pinna 960 associated with a respective non-linear transfer function 958 to an image of the pinna associated with reference sensor output 962. This comparison may be assigned a first correlation score. Additionally, the comparator 954 may be arranged to compare the frequency responses of a respective non-linear transfer function 958 to the detected respective second sound by each of the one or more microphones associated with reference sensor output 962. This comparison may be assigned a second correlation score. The respective correlation scores for a same non-linear transfer function may be combined, e.g., summed, to form a combined score. The comparator 954 may output a non-linear transfer function 958 of the plurality of non-linear transfer functions which has a highest combined score as the non-linear transfer function 964.

In this regard, the direct measurement may not need to be performed on the pinna of the individual to determine the non-linear transfer function 964. Instead, the non-linear transfer function 964 may be based on the plurality of non-linear transfer functions determined during the learning process and stored and the database 952 and used in real time to determine the non-linear transfer function 964.

The non-linear transfer function 964 may be the non-linear transfer function which is modulated at step 706. In this regard, the direct measurement may not need to be performed on the pinna of the individual for whom the audio cues are to be generated at 706 to determine the non-linear transfer function 962. Instead, the non-linear transfer function 964 may be based on the plurality of non-linear transfer functions determined during the learning process and stored in the database 952 and used in real time to determine the non-linear transfer function 964.

In some examples, the non-linear transfer function 962 for the individual for whom the audio cues are to be generated at 706 may be based on a combination of one or more of the plurality of non-linear transfer functions stored in the database 952. For instance, one or more of the plurality of non-linear transfer functions may be weighed to determine non-linear transfer function 964.

The weighting may be based on a classification, e.g., closeness or similarity of match, between the detected respective second sounds associated with the reference sensor output 962 and the frequency responses of the non-linear transfer function 958 of the plurality of non-linear transfer functions. For instance, a closer match may result in a stronger weighting while a farther match may result in a weaker weighting. Then, the weighed non-linear transfer functions may be combined, e.g., summed, to form the non-linear transfer function 962 associated with step 706.

Figure 9E:
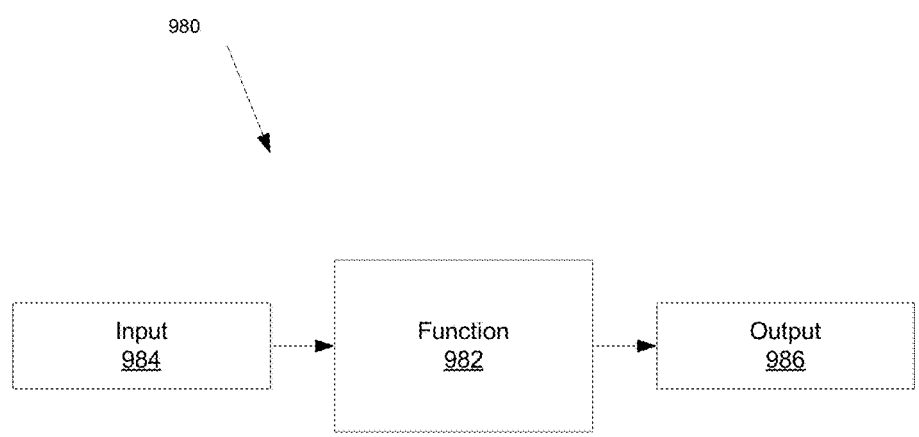

FIG. 9E illustrates another example arrangement 980 for determining the non-linear transfer function for the individual for which audio cues is to be determined at 706. The plurality of non-linear transfer functions and/or associated image of the pinna determined during the learning process may be parameterized via numerical analysis methods to define a function 982 with an input 984 and output 986. The input 984 to the function 982 may be an image of the pinna and/or detected respective second sound associated with the reference sensor output 962 and the output 986 of the function 982 may be a non-linear transfer function. The function may take a variety of forms.

For instance, the function 982 may take the form of a model fit to the plurality of non-linear transfer functions and/or associated images of a pinna determined during the learning phase using well known data fitting techniques such as neural networks. An input in the form of an image of the pinna captured by an image sensor for the individual for whom the audio cues are to be generated at 706 may be input into the model and the model may output a non-linear transfer function for the input. Additionally, or alternatively, an input in the form of the detected respective second sound associated with the reference sensor output 962 may be input into the model and the model may output a non-linear transfer function for sensor output. The output may be the non-linear transfer function which is modulated at step 706.

Further details for determining the non-linear transfer function for the individual wearing the personal audio delivery device are described in U.S. application Ser. No. 15/811,295, entitled "Image and Audio Based Characterization of a Human Auditory System for Personalized Audio Reproduction" filed on Nov. 13, 2017, the contents of which are herein incorporated by reference in their entirety.

In some cases, the sound detected by the microphone at 702 may include sound output by the transducer. This may occur due to an inherent sensitivity of the microphone even though microphone might be directed away from the pinna and/or transducer. The processing engine may cancel out this sound output by the transducer before modulation. Well known echo cancellation techniques may be used to perform this cancellation. Alternatively, the processing engine may cancel out this sound output by the transducer during the modulation process. Other variations are also possible.

At 708, a third signal is received by the processing engine indicative of sound to be output by the personal audio delivery device. The personal audio delivery device may output sound to the human auditory system via the transducer. The sound might be music, voice, or other content. The second signal may be received from a storage device or even generated by the processing device itself. The second signal may be representative of this sound.

At 710, the second signal (e.g., modulated signal) may be mixed with the third signal. The mixed signal may allow a user to hear the sound output by the personal audio delivery device as well as audio cues associated with the real-world sound so as to facilitate spatialization of the real-world sound.

The second signal may be mixed with the third signal in various proportions. The proportion that the second signal is mixed with the third signal may be based on a user setting. In one example, the second and third signals may be mixed such that the user will hear the one or more audio cues louder than sound associated with the third signal. For instance, the second signal may be weighed more than the third signal and then summed together to form the mixed signal. In another example, the second and third signals may be mixed such that the user will hear the one or more audio cues less than sound associated with the third signal. For instance, the second signal may be weighed less than the third signal and then summed together to form the mixed signal. In yet another example, the weighting may be based on the type of detected sound. For example, the processing engine may determine whether the detected sound is associated with a vehicle such as a siren or car horn. This determination may be performed via a classification and training process such that the algorithm provides an indication that the detected sound is associated with the vehicle. Based on this determination, the second signal may be weighed more than the third signal to make a user spatially aware of the sound. Other variations are also possible.

At 708, the mixed signal is output by the earcup of the personal audio delivery device to facilitate the spatial localization of the detected sound based on the one or more audio cues while the earcup is worn on the pinna. The mixed signal may be input into the transducer and the transducer converts the signal to audible sound. The mixed signal may artificially generate missing audio cues so that a user can perceive a direction where the real-world sound comes from even though the earcup of the personal audio delivery device may be covering the pinna. As a result, a person may be spatially aware of sounds in his surroundings while wearing the personal audio delivery device. For example, the person wearing the personal audio delivery device while walking through a busy intersection can not only hear sound of cars around him but also perceive a direction where the sound of the car is coming from. This may improve the safety of the user when wearing the personal audio delivery devices. Further, this perception may be possible whether or not the personal audio delivery device also outputs sound other than associated with the real-world sound, e.g., music.

The processing associated with steps 702-712 may be performed for each earcup. One earcup may be seated on a left ear and another earcup may be seated on a right ear. In this regard, the left earcup may output respective audio cues for spatial localization at the left ear and the right earcup may output respective audio cues for spatial localization at the right ear. However, in other examples, respective signals output by each microphone may be combined together and this combined signal may be processed in accordance steps 704-712. In this case, each earcup may output same audio cues. Other variations are also possible.

In some examples, the audio cues may be output by the earcup without performing the steps associated with steps 708 and 710. In this case, the personal audio delivery device may simply output the audio cues to facilitate spatial localization of the detected sound associated with the first signal.

Further, in some examples, the mixing at step 710 may be performed as part of the modulation process at step 706 rather than as a subsequent step to the modulation. The non-linear transfer function, first signal, and second signal may be combined in other ways as well.

The description above discloses, among other things, various example systems, methods, apparatus, and articles of manufacture including, among other components, firmware and/or software executed on hardware. It is understood that such examples are merely illustrative and should not be considered as limiting. For example, it is contemplated that any or all of the firmware, hardware, and/or software aspects or components can be embodied exclusively in hardware, exclusively in software, exclusively in firmware, or in any combination of hardware, software, and/or firmware. Accordingly, the examples provided are not the only way(s) to implement such systems, methods, apparatus, and/or articles of manufacture.

Additionally, references herein to "example" and/or "embodiment" means that a particular feature, structure, or characteristic described in connection with the example and/or embodiment can be included in at least one example and/or embodiment of an invention. The appearances of this phrase in various places in the specification are not necessarily all referring to the same example and/or embodiment, nor are separate or alternative examples and/or embodiments mutually exclusive of other examples and/or embodiments. As such, the example and/or embodiment described herein, explicitly and implicitly understood by one skilled in the art, can be combined with other examples and/or embodiments. Further, reference to a microphone can refer to one microphone or more than one microphone such as an array of microphones.

The specification is presented largely in terms of illustrative environments, systems, procedures, steps, logic blocks, processing, and other symbolic representations that directly or indirectly resemble the operations of data processing devices coupled to networks. These process descriptions and representations are typically used by those skilled in the art to most effectively convey the substance of their work to others skilled in the art. Numerous specific details are set forth to provide a thorough understanding of the present disclosure. However, it is understood to those skilled in the art that certain embodiments of the present disclosure can be practiced without certain, specific details. In other instances, well known methods, procedures, components, and circuitry have not been described in detail to avoid unnecessarily obscuring aspects of the embodiments. Accordingly, the scope of the present disclosure is defined by the appended claims rather than the forgoing description of embodiments.

When any of the appended claims are read to cover a purely software and/or firmware implementation, at least one of the elements in at least one example is hereby expressly defined to include a tangible, non-transitory medium such as a memory, DVD, CD, Blu-ray, and so on, storing the software and/or firmware.

EXAMPLE EMBODIMENTS

Example embodiments include:

Embodiment 1

A method comprising: receiving a signal indicative of sound detected by at least one sensor of an audio device, wherein the audio device at least partially covers a pinna and wherein the detected sound interacts with at least a torso of a body; modulating the signal with a non-linear transfer function to generate a modulated signal indicative of one or more audio cues to facilitate spatialization of the detected sound while the audio device at least partially covers the pinna; and outputting, by the audio device, the modulated signal.

Embodiment 2

The method of Embodiment 1, wherein the signal indicative of the sound detected by the at least one sensor is a first signal, and wherein outputting, by the audio device, the modulated signal comprises mixing the modulated signal with a second signal.

Embodiment 3

The method of Embodiment 1 or 2, wherein mixing the modulated signal with the second signal comprises weighing the modulated signal and the second signal during the mixing based on a sound type of the detected sound.

Embodiment 4

The method of any of Embodiments 1-3, wherein receiving the first signal indicative of sound detected by at least one sensor at the audio device comprises receiving the first signal indicative of the sound detected by at least one microphone at the audio device.

Embodiment 5

The method of any of Embodiments 1-4, wherein the at least one microphone is directed away from the pinna.

Embodiment 6

The method of any of Embodiments 1-5, wherein the one or more audio cues is based on one or more of an elevation, azimuth, distance, and velocity of a sound source associated with the detected sound.

Embodiment 7

The method of any of Embodiments 1-6, wherein modulating the signal with the non-linear transfer function comprises determining a direction where the detected sound is coming from and identifying one or more waveforms of the non-linear transfer function associated with the direction.

Embodiment 8

The method of any of Embodiments 1-7, further comprising: comparing a frequency response of the pinna to frequency responses of other pinna, wherein each frequency response of the other pinna is associated with a respective non-linear transfer function; determining one of the other frequency responses of the other pinna which is closest to the frequency response based on the comparison; and identifying the non-linear transfer function as the respective non-linear transfer function associated with the one of the other frequency responses.

Embodiment 9

One or more non-transitory computer readable media comprising program code stored in memory and executable by a processor, the program code to: receive a signal indicative of sound detected by at least one sensor of an audio device, wherein the audio device at least partially covers a pinna and wherein the detected sound interacts with at least a torso of a body, modulate the signal with a non-linear transfer function to generate a modulated signal indicative of one or more audio cues to facilitate spatialization of the detected sound while the audio device at least partially covers the pinna, and output, by the audio device, the modulated signal.

Embodiment 10

The one or more non-transitory machine-readable media of Embodiment 9, wherein the signal indicative of the sound detected by the at least one sensor is a first signal; and wherein the program code to output, by the audio device, the modulated signal comprises mixing the modulated signal with a second signal.

Embodiment 11

The one or more non-transitory machine-readable media of Embodiment 9 or 10, wherein the program code to mix the modulated signal with the second signal comprises weighing the modulated signal and the second signal during the mixing based on a sound type of the detected sound.

Embodiment 12

The one or more non-transitory machine-readable media of Embodiment 10 or 11, wherein the program code to receive the first signal indicative of sound detected by at least one sensor at the audio device comprises receiving the first signal indicative of the sound detected by at least one microphone at the audio device.

Embodiment 13

The one or more non-transitory machine-readable media of any of Embodiments 10-12, wherein the at least one microphone is directed away from the pinna.

Embodiment 14

The one or more non-transitory machine-readable media of any of Embodiments 10-13, wherein the one or more audio cues is based on one or more of an elevation, azimuth, distance, and velocity of a sound source associated with the detected sound.

Embodiment 15

The one or more non-transitory machine-readable media of any of Embodiments 10-14, wherein the program code to modulate the signal with the non-linear transfer function comprises to determining a direction where the detected sound is coming from and identifying one or more waveforms of the non-linear transfer function associated with the direction.

Embodiment 16

The one or more non-transitory machine-readable media of any of Embodiments 10-15, wherein the program code former comprises comparing a frequency response of the pinna to frequency responses of other pinna, wherein each frequency response of the other pinna is associated with a respective non-linear transfer function; determining one of the other frequency responses of the other pinna which is closest to the frequency response based on the comparison; and identifying the non-linear transfer function as the respective non-linear transfer function associated with the one of the other frequency responses which is closest to the frequency response.

Embodiment 17

A system comprising: an audio device; computer instructions stored in memory and executable by a processor to perform the functions of: receiving a signal indicative of sound detected by at least one sensor of the audio device, wherein the audio device at least partially covers a pinna and wherein the detected sound interacts with at least a torso of a body; modulating the signal with a non-linear transfer function selected based on the direction of the sound to generate a modulated signal indicative of one or more audio cues to facilitate spatialization of the detected sound while the audio device at least partially covers the pinna; and outputting, by the audio device, the modulated signal.

Embodiment 18

The system of Embodiment 17, wherein the computer instructions stored in memory and executable by the processor for modulating the signal with the non-linear transfer function comprises determining a direction where the detected sound is coming from and identifying one or more waveforms of the non-linear transfer function associated with the direction.

Embodiment 19

The system of Embodiment 17 or 18, further comprising computer instructions stored in memory and executable by the processor to: compare a frequency response of the pinna to frequency responses of other pinna, wherein each frequency response of the other pinna is associated with a respective non-linear transfer function; determine one of the other frequency responses of the other pinna which is closest to the frequency response based on the comparison; and identify the non-linear transfer function as the respective non-linear transfer function associated with the one of the other frequency responses which is closest to the frequency response.

Embodiment 20

The system of any of Embodiments 17-19, wherein the one or more audio cues indicates one or more of an elevation, distance, azimuth, and velocity of a sound source associated with the detected sound.

I claim:

1. A method comprising:
receiving a signal indicative of sound detected by at least one sensor of an audio device, wherein the audio device at least partially covers a pinna and wherein the detected sound interacts with at least a torso of a body;
modulating the signal with a non-linear transfer function to generate a modulated signal indicative of one or more audio cues to facilitate spatialization of the detected sound while the audio device at least partially covers the pinna;
determining a sound type of the detected sound;
mixing the modulated signal with a signal indicative of audio to be output by the audio device, wherein the modulated signal is weighted in the mixing based on the determined sound type; and
outputting, by the audio device, the mixed modulated signal.

2. The method of claim 1, wherein receiving the signal indicative of sound detected by at least one sensor at the audio device comprises receiving the signal indicative of the sound detected by at least one microphone at the audio device.

3. The method of claim 2, wherein the at least one microphone is directed away from the pinna.

4. The method of claim 1, wherein the one or more audio cues is based on one or more of an elevation, azimuth, distance, and velocity of a sound source associated with the detected sound.

5. The method of claim 1, wherein modulating the signal with the non-linear transfer function comprises determining a direction where the detected sound is coming from and identifying one or more waveforms of the non-linear transfer function associated with the direction.

6. The method of claim 1, further comprising:
comparing a frequency response of the pinna to frequency responses of other pinna, wherein each frequency response of the other pinna is associated with a respective non-linear transfer function;
determining one of the other frequency responses of the other pinna which is closest to the frequency response based on the comparison; and
identifying the non-linear transfer function as the respective non-linear transfer function associated with the one of the other frequency responses.

7. One or more non-transitory machine-readable media comprising program code stored in memory and executable by a processor, the program code to:
receive a signal indicative of sound detected by at least one sensor of an audio device, wherein the audio device at least partially covers a pinna and wherein the detected sound interacts with at least a torso of a body;
modulate the signal with a non-linear transfer function to generate a modulated signal indicative of one or more audio cues to facilitate spatialization of the detected sound while the audio device at least partially covers the pinna;
determining a sound type of the detected sound;
mixing the modulated signal with a signal indicative of audio to be output by the audio device, wherein the modulated signal is weighted in the mixing based on the determined sound type; and
output, by the audio device, the mixed modulated signal.

8. The one or more non-transitory machine-readable media of claim 7, wherein the program code to receive the signal indicative of sound detected by at least one sensor at the audio device comprises receiving the signal indicative of the sound detected by at least one microphone at the audio device.

9. The one or more non-transitory machine-readable media of claim 8, wherein the at least one microphone is directed away from the pinna.

10. The one or more non-transitory machine-readable media of claim 7, wherein the one or more audio cues is based on one or more of an elevation, azimuth, distance, and velocity of a sound source associated with the detected sound.

11. The one or more non-transitory machine-readable media of claim 7, wherein the program code to modulate the signal with the non-linear transfer function comprises determining a direction where the detected sound is coming from and identifying one or more waveforms of the non-linear transfer function associated with the direction.

12. The one or more non-transitory machine-readable media of claim 7, wherein the program code further comprises:
comparing a frequency response of the pinna to frequency responses of other pinna, wherein each frequency response of the other pinna is associated with a respective non-linear transfer function;

determining one of the other frequency responses of the other pinna which is closest to the frequency response based on the comparison; and identifying the non-linear transfer function as the respective non-linear transfer function associated with the one of the other frequency responses which is closest to the frequency response.

13. A system comprising:

an audio device;
    computer instructions stored in memory and executable by a processor to perform the functions of:
        receiving a signal indicative of sound detected by at least one sensor of the audio device, wherein the audio device at least partially covers a pinna and wherein the detected sound interacts with at least a torso of a body;
        modulating the signal with a non-linear transfer function selected based on the direction of the sound to generate a modulated signal indicative of one or more audio cues to facilitate spatialization of the detected sound while the audio device at least partially covers the pinna;
        determining a sound type of the detected sound;
        mixing the modulated signal with a signal indicative of audio to be output by the audio device, wherein the modulated signal is weighted in the mixing based on the determined sound type; and
        outputting, by the audio device, the mixed modulated signal.

14. The system of claim 13, wherein the computer instructions stored in memory and executable by the processor for modulating the signal with the non-linear transfer function comprises determining a direction where the detected sound is coming from and identifying one or more waveforms of the non-linear transfer function associated with the direction.

15. The system of claim 13, further comprising computer instructions stored in memory and executable by the processor to:
    compare a frequency response of the pinna to frequency responses of other pinna, wherein each frequency response of the other pinna is associated with a respective non-linear transfer function;
    determine one of the other frequency responses of the other pinna which is closest to the frequency response based on the comparison; and
    identify the non-linear transfer function as the respective non-linear transfer function associated with the one of the other frequency responses which is closest to the frequency response.

16. The system of claim 13, wherein the one or more audio cues indicates one or more of an elevation, distance, azimuth, and velocity of a sound source associated with the detected sound.

17. The method of claim 1, wherein the modulated signal is weighted more than the signal indicative of audio to be output by the audio device in the mixing.

* * * * *